United States Patent [19]

Rieck

[11] 4,438,081
[45] Mar. 20, 1984

[54] PROCESS FOR THE PURIFICATION OF CYCLIC CHLOROPHOSPHAZENES

[75] Inventor: Hans-Peter Rieck, Kelkheim, Fed. Rep. of Germany

[73] Assignee: Hoechst Aktiengesellschaft, Fed. Rep. of Germany

[21] Appl. No.: 437,882

[22] Filed: Oct. 29, 1982

[30] Foreign Application Priority Data

Nov. 11, 1981 [DE] Fed. Rep. of Germany ....... 3144751

[51] Int. Cl.$^3$ .............................................. C01B 25/10
[52] U.S. Cl. .................................... 423/300; 423/299
[58] Field of Search ................................ 423/300, 299

[56] References Cited

FOREIGN PATENT DOCUMENTS 38-8302 7/1963 Japan ................................... 423/300

Primary Examiner—Gregory A. Heller
Attorney, Agent, or Firm—Berman, Aisenberg & Platt

[57] ABSTRACT

Oligomeric chlorophosphazenes of the formula $$(N=PClR)_n$$

in which n is an integer of from 3 to 8 and R is phenyl, $C_1$–$C_6$-alkyl or chlorine, are treated with sulfur dioxide or sulfur oxide chlorides, and so purified. The chlorophosphazene is for example recrystallized with a sulfur oxide chloride.

16 Claims, No Drawings

PROCESS FOR THE PURIFICATION OF CYCLIC CHLOROPHOSPHAZENES

The present invention provides a process for the purification of cyclic chlorophosphazenes which may be substituted by alkyl or phenyl groups, by treating them with sulfur dioxide or sulfur oxide chlorides.

The main application field of oligomeric cyclic chlorophosphazenes (oligomerization degree n=3–8) is their polymerization to yield polymeric chlorophosphazenes which after subsequent reaction with alcoholates, especially perfluoro-alcoholates, give low temperature elastomers stable to hydrolysis. This polymerization is carried out at about 250° C. and results in a mixture in which in addition to the polymer (polymerization degree m=3–50,000) the starting oligomer is still present. The reactions proceed according to the following scheme:

in which $R^1$ is alkyl, perfluoroalkylmethyl or aryl, and R is alkyl or aryl, or may be chlorine. In the latter case, R is replaced by $OR^1$ in the reaction with alcoholate. The polymerization can be carried out with the use of one oligomer alone or a mixture of different oligomers.

Oligomeric chlorophosphazenes can be purified according to various methods, for example by fractional crystallization with the use of especially aliphatic hydro-carbons as solvents (H. R. Allcock, Phosphorus-Nitrogen Compounds, New York 1972, p. 309). In principle, however, other solvents are appropriate, too (U.S. Pat. No. 3,378,353). Discoloration of the oligomeric phosphazenes can be obtained in some cases by using active charcoal.

It has been observed that in many cases in the thermal polymerization oligomeric chlorophosphazenes react to become dark-brown products containing a large amount of compounds which are insoluble in organic solvents. This is often the case even when starting from pure oligomers, that is, a pure trimer having a purity degree of 99 or 99.9%. It is, however, required that a small amount only of insoluble compounds is formed and that the color of the reaction products remains light, because from such a reaction product only light-colored low temperature elastomers especially in demand in the industrial practice can be obtained in the further reaction with alcoholates.

It was therefore the object of the invention to provide a process by means of which oligomers can be simply purified in such a manner that on polymerization they yield masses which can be further processed. This process moreover should apply to oligomer mixtures as well as to one oligomer alone.

In accordance with the invention, there has been found a process for the purification of oligomeric chlorophosphazenes of the formula

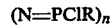

in which n is an integer of from 3 to 8, and R is phenyl, $C_1$–$C_6$-alkyl, or chlorine, which comprises treating the oligomeric chlorophosphazene with sulfur dioxide or a sulfur oxide chloride.

This process ensures that a change of color in the subsequent polymerization, especially by heating the oligomeric chlorophosphazene in the thermal polymerization, is substantially suppressed or very often completely prevented. The chlorophosphazenes can be treated by introducing sulfur dioxide into solutions or melts, by addition of the sulfur oxide chlorides to solutions of the phosphazene, by dissolving the phosphazene in the sulfur oxide chloride, or by a corresponding intermixing with stirring. Treatment in the liquid phase is preferred.

As sulfur oxide chlorides, thionyl chloride or sulfuryl chloride, especially thionyl chloride, are preferably used in liquid or gaseous, pure or dilute form.

Sulfuryl chloride and thionyl chloride are nonflammable; due to their favorable boiling point of 69° C. and 79° C., respectively, they can be easily separated again from the cyclic chlorophosphazenes. Since the solubility of the chlorophosphazenes in the above sulfur oxide chlorides depends on the temperature chosen, these chlorides are a suitable medium for recrystallization.

It is recommended to combine the treatment of the chlorophosphazenes with sulfur oxide chlorides according to the invention with other purification methods, such as distillation, washing with water, or crystallization. Thus, it is advantageous to distil or sublime the chlorophosphazene after the treatment with the sulfur oxide chloride or sulfur dioxide, although another sequence is possible, too. It is alternatively recommended to treat the crude phosphazene first with water, to dry distil it, and to treat it then with sulfur oxide chlorides or $SO_2$. It is advantageous that the sulfur oxide chlorides react with water, that is, act as strong dehydrating agents. Especially thionyl chloride is highly suitable for this purpose, because its hydrolysis products $SO_2$ and HCl, being gaseous substances, can be easily removed from the reaction mixture.

The following examples illustrate the invention.

EXAMPLE 1

(Comparative Example)

Phosphorus pentachloride and ammonium chloride in chlorobenzene are reacted to give a mixture of cyclic dichlorophosphazenes. The crude product is extracted with water for 15 minutes at 90° C., the chlorobenzene-containing phase is separated, and the crude product is subjected to fractional distillation via a packed column. Trimer dichlorophosphazene $(NPCl_2)_3$ having a purity degree of more than 99% according to gas chromatography is obtained. A sample is melted in a glass tube under a pressure of less than 13 Pa, and heated for 21 hours at 270°–280° C. After one hour, the sample becomes slightly brownish; after 4½ hours it has a distinct light brown color, and finally it has an intense dark brown color. During the complete period of time, it is fluid at elevated temperature, and solidifies at room temperature to give a crystalline solid matter. Polymerization is complete therefore to a very small extent only.

EXAMPLE 2

Distilled $(NPCl_2)_3$ of Example 1 is recrystallized with thionyl chloride and, as described in Example 1, melted in a glass tube and treated thermally. After 21 hours at 270°–280° C., the dichlorophosphazene has a very light tint of brownish color. It is fluid at elevated temperatures and crystallizes at low temperature.

EXAMPLE 3

The phosphazene recrystallized from thionyl chloride according to Example 2 is sublimed and subsequently melted in a glass tube and thermally treated as indicated in Example 1. After 21 hours at 270°–280° C. the dichlorophosphazene remains completely colorless, is a viscous liquid at elevated temperatures and solidified at room temperature to a polymer which is turbid due to crystallized portions.

EXAMPLE 4

Distilled $(NPCl_2)_3$ of Example 1 as dissolved in chlorobenzene. $SO_2$ is introduced into the solution for 15 minutes at 30°–50° C. The solvent is distilled off under reduced pressure, the phosphazene is sublimed and treated as indicated in Example 1. After 21 hours at 270°–280° C. the product remains completely colorless, is not fluid at elevated temperatures, and becomes glassy at room temperature. The polymerization is therefore complete to a far greater extent than in Example 1.

EXAMPLE 5

100 mg of $AlCl_3$ are added to 10 g of the product of Example 3. The mixture is thermally treated as indicated in Example 1. After 21 hours at 270°–280° C. the product is a slightly brownish liquid highly viscous at elevated temperatures.

EXAMPLE 6

About 10 mg of water are added to 10 g of sublimed product of Example 3, and the mixture is treated as indicated in Example 1. After 21 hours at 270°–280° C. the product is completely colorless, non-fluid at elevated temperatures, and contains small fluid portions.

EXAMPLE 7

According to German Offenlegungsschrift No. 2,940,389, methyldichlorophosphane, chlorine and ammonium chloride are converted to a mixture of oligomeric methylchlorophosphazenes $(NPCH_3Cl)_n$. The product contains small amounts of a methylchlorophosphazene in which a small amount of the hydrogen atoms is replaced by chlorine. The product mixture is recrystallized with thionyl chloride, the solids are sublimed at 13 Pa, melted under the same pressure in a glass tube, and subsequently heated to 230° C. The product changes its color only slowly. When, however, the methylchlorophosphazene is recrystallized from another solvent, such as heptane, instead of from thionyl chloride, the change of color is considerably more intense and very rapid on thermal polymerization.

What is claimed is:

1. A process of substantially suppressing or completely preventing a change of color during polymerization of an oligomeric chlorophosphazene of the formula $$(N=PClR)_n$$

in which n is an integer of from 3 to 8, and
R is phenyl, $C_1$–$C_6$-alkyl, or chlorine, which comprises treating the oligomeric chlorophosphazene with sulfur dioxide or a sulfur oxide chloride.

2. The process as claimed in claim 1, which comprises recrystallizing the chlorophosphazene with a sulfur oxide chloride.

3. The process as claimed in claim 1, wherein the sulfur oxide chloride is thionyl chloride.

4. The process as claimed in claim 2, wherein the sulfur oxide chloride is thionyl chloride.

5. A process according to claim 1 wherein R is phenyl.

6. A process according to claim 1 wherein R is $C_1$–$C_6$-alkyl.

7. A process according to claim 1 wherein R is chlorine.

8. A process for purifying an oligomeric chlorophosphazene of the formula $$(N=PCl_2)_n$$

in which n is an integer of from 3 to 8, which comprises extracting the oligomeric chlorophosphazene with water and treating
   (a) a solution of the chlorophosphazene in a solvent or
   (b) a melt of the chlorophosphazene with $SO_2$ by introducing gaseous $SO_2$ and isolating the oligomeric chlorophosphazene.

9. A process according to claim 8 which comprises treating the solution of the chlorophosphazene in a solvent.

10. A process according to claim 9 wherein the solvent is chlorobenzene.

11. A process according to claim 8 wherein the oligomeric chlorophosphazene is distilled after the extraction with water and prior to treatment with $SO_2$.

12. A process according to claim 8 which comprises treating a melt of the chlorophosphazene with $SO_2$.

13. A process for purifying an oligomeric chlorophosphazene of the formula $$(N-PCl_2)_n$$

in which n is an integer of from 3 to 8, which comprises recrystallizing the chlorophosphazene from a sulfur compound selected from the group consisting of $SOCl_2$ and $SO_2Cl_2$.

14. A process according to claim 13 wherein the sulfur compound is $SOCl_2$.

15. A process according to claim 13 wherein the sulfur compound is $SO_2Cl_2$.

16. A process according to claim 13 wherein the chlorophosphazene is extracted with water and distilled prior to recrystallization.

* * * * *